United States Patent [19]

Bernstein

[11] Patent Number: 4,949,734

[45] Date of Patent: Aug. 21, 1990

[54] SHIELD FOR ELECTROSURGICAL DEVICE

[76] Inventor: Gerald Bernstein, 6653 N.E. Windermere Rd., Seattle, Wash. 98115

[21] Appl. No.: 236,501

[22] Filed: Aug. 25, 1988

[51] Int. Cl.$^5$ .............................................. A61G 17/00
[52] U.S. Cl. ........................................ 128/897; 606/32
[58] Field of Search ........... 128/303.1, 303.11–303.19, 128/846, 847; 604/162, 192, 283; 219/121.43; 606/32, 41–52

[56] References Cited

U.S. PATENT DOCUMENTS

| | | |
|---|---|---|
| 2,032,859 | 3/1936 | Wappler ........................ 128/303.11 |
| 2,102,270 | 12/1937 | Hyams . |
| 2,196,171 | 4/1940 | Arnesen . |
| 2,275,167 | 3/1942 | Bierman . |
| 2,808,833 | 10/1957 | August . |
| 2,888,928 | 6/1959 | Seiger . |
| 3,035,580 | 5/1962 | Guiorguiev . |
| 3,595,239 | 7/1971 | Peterson . |
| 3,614,414 | 10/1971 | Gores . |
| 3,648,001 | 3/1972 | Anderson et al. . |
| 3,801,766 | 4/1974 | Morrison, Jr. . |
| 3,828,780 | 8/1974 | Morrison, Jr. . |
| 3,847,153 | 11/1974 | Weissman . |
| 3,906,955 | 9/1975 | Roberts . |
| 3,920,022 | 11/1975 | Pastor . |
| 3,939,839 | 2/1976 | Curtiss ........................... 128/303.15 |
| 3,974,833 | 8/1976 | Durden, III . |
| 4,074,718 | 2/1978 | Morrison, Jr. . |
| 4,449,528 | 5/1984 | Auth et al. . |
| 4,562,838 | 1/1986 | Walker .............................. 14/303.14 |
| 4,643,186 | 2/1987 | Rosen et al. ................... 128/303.13 |
| 4,719,914 | 1/1988 | Johnson . |

Primary Examiner—Lee S. Cohen
Assistant Examiner—David Shay
Attorney, Agent, or Firm—Christensen, O'Connor, Johnson & Kindness

[57] ABSTRACT

A transparent shield for the electrode of an electrosurgical device. The shield is designed to prevent the spray of blood and splatter of tissue generated during electrosurgery from being deposited upon the surgeon using the device and is particularly adapted to protect the face and eyes of the surgeon against contact by such airborne fluids and particles. The shield is adapted to be mounted upon a wide variety of electrodes or electrosurgical instruments and may be curved for use with curved electrodes. The shield may also be curved in the transverse direction along its length to better confine spray and splatter.

22 Claims, 1 Drawing Sheet

SHIELD FOR ELECTROSURGICAL DEVICE

FIELD OF THE INVENTION

This invention relates to electrosurgical units in general and, in particular, to a shield mountable adjacent the electrode of an electrosurgical unit to prevent the spray and splatter of blood and tissue generated during electrosurgery, fulguration, desiccation or cauterization from being deposited upon the surgeon using the electrosurgical unit or the surgical assistants.

BACKGROUND OF THE INVENTION

Electrosurgery, including both the cutting of tissue and the coagulation of vessels, has been performed for many decades. A typical electrosurgical unit such as the Hyfrecator ® manufactured by Birtcher Corporation of El Monte, Calif., has been manufactured and sold for more than fifty years. Typical electrosurgical units in current use such as the Birtcher unit or the Electricator TM offered for sale by Burton Medical Products, of Van Nuys, Calif., include a control console having a current selection control and a current intensity control and a pen-type active electrode holder mounted on the end of an electrical cable connected to the control console.

Electrodes of either the disposable or reusable type are mounted in the pen-type holder, which is then gripped by the surgeon and manipulated to perform the desired cutting or coagulation task. A sampling of electrosurgical units and their operation are described in U.S. Pat. Nos. 2,102,270; 2,275,167; 2,808,833; and 2,888,928.

During the cutting or cauterization of tissue, smoke is often produced and U.S. Pat. Nos. 3,828,780; 3,906,955; 3,974,833; 4,562,838 and 4,719,914 disclose the use of streams of air or vacuum suction to remove smoke from the area of contact between the active electrode and the patient to improve the surgeon's view of the work area. None of the above-listed prior art patents, however, have provided solutions to the serious problem of the spray and splatter of blood and tissue which emanate from the work area during use of an electrosurgical tool.

It will be understood that, as with all fine scale work, there is a tendency and need for a surgeon to place his face in relatively close proximity to the work area where the active electrode contacts the patient's skin in order to obtain the best view of the area. This has often resulted in blood or tissue particles being sprayed or splattered onto the surgeon's face or into his eyes. Some passive protection has been provided the surgeon through the wearing of glasses and surgical masks, but electrode holders themselves have not been provided with means for preventing the travel of spray and splatter toward the surgeon or his assistants.

SUMMARY OF THE INVENTION

The present invention provides a shield that is removably mountable upon a wide variety of shapes and sizes of electrodes and electrosurgical units, such that a transparent spray and splatter barrier is positioned between the work area where the active electrode contacts the patient's skin and the face and eyes of the surgeon using the electrosurgical unit. The spray shield includes a transparent barrier extending along the length of the electrode and positioned at a relatively close distance therefrom so as to be able to capture spray or splatter generated during use of the electrosurgical device while, at the same time, not hindering the surgeon's ability to manipulate the electrode at the work surface without causing the shield to contact the patient.

In one embodiment, the shield is curved to conform to the general shape of electrodes that are curved along their length and is also curved in a transverse direction along the electrode's length to better capture spray and splatter. The shield of the present invention is preferably a single molded piece formed of a transparent material that allows a surgeon to view the work area through the shield. The integral mounting means for the shield is adapted to resiliently clamp the electrode, its insulator, or the pen-style electrode holder such that the transparent barrier end of the shield is generally adjacent the work area.

DETAILED DESCRIPTION OF THE INVENTION

Figures 1, 2, 3, 4, 5:
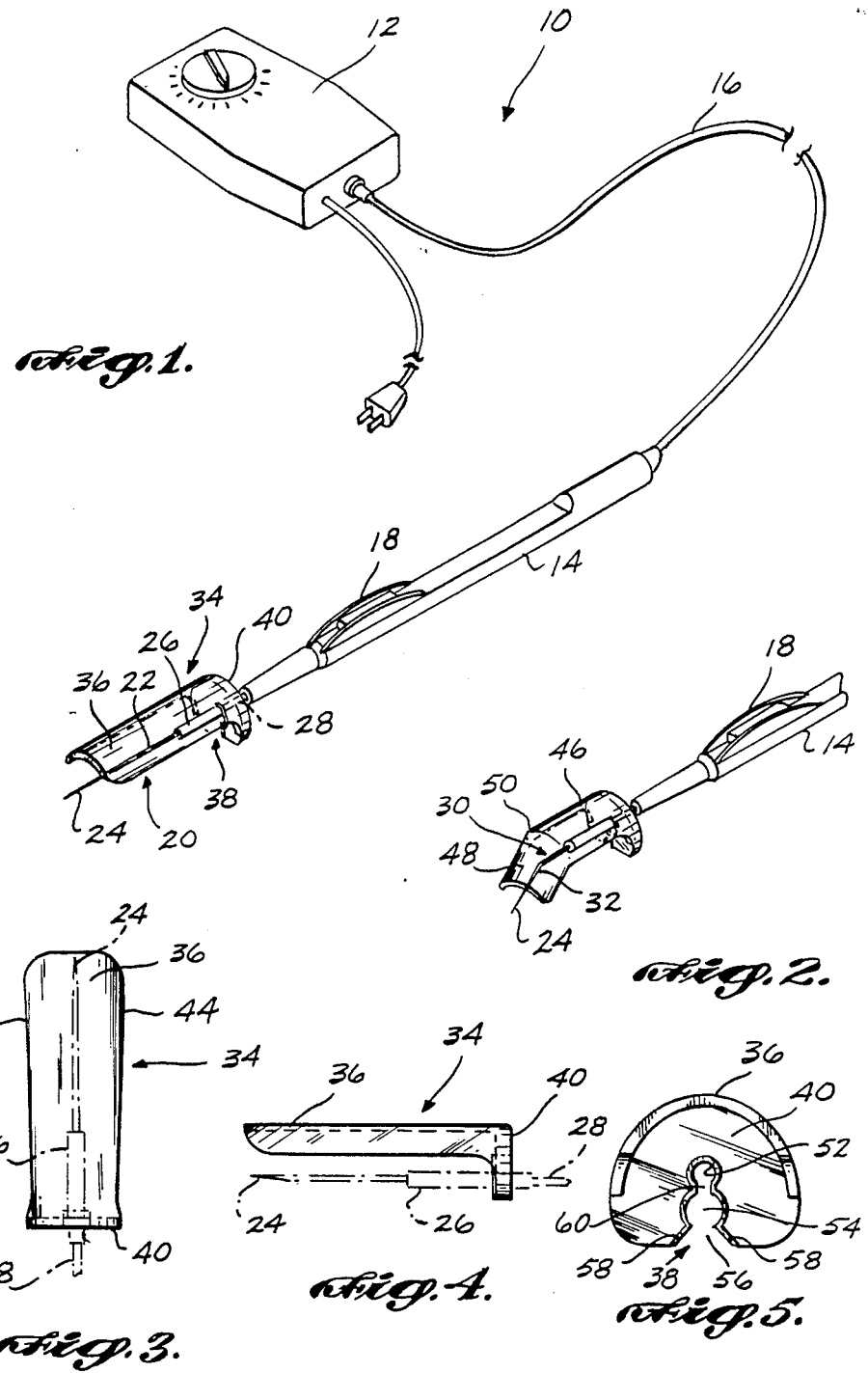
FIG. 1 is a partial perspective view of a typical electrosurgical unit showing the spray shield of the present invention mounted on the electrode thereof.
FIG. 2 is a partial perspective view of the electrosurgical unit of FIG. 1 showing an alternate embodiment of the spray shield of the present invention curved to conform to the shape of a curved electrode mounted in the electrode holder.
FIG. 3 is a top view of the spray shield of the present invention mounted on a medical electrode and showing the transverse curve of the transparent barrier means being flattened along its length toward the electrode end.
FIG. 4 is a side elevation view of a spray shield made according to the present invention.
FIG. 5 is an elevation view of the mounting end of the spray shield of the present invention showing one embodiment of a mounting means of the present invention.

Referring initially to FIG. 1, an electrosurgical unit 10 is disclosed including a conventional control console 12, and a hand-held, pen-type electrode holder 14 interconnected therewith by means of a conventional power cable 16. Electrode holder 14 includes a switch 18 whereby the surgeon using the device is able to control the application of electrical power to the cutting or cauterizing electrode 20. In an alternate embodiment, the application of power to the electrode may be controlled through activation of a conventional foot control.

Electrodes suitable for mounting on electrode holder 14 come in a wide variety of specialized shapes and sizes for performing a wide variety of medical tasks. In general, however, the electrodes include an elongate metal, electrically conductive portion 22 having a working tip portion 24, an insulator portion 26, and a means 28 for connecting the electrode to electrode holder 14. Electrodes commonly have a needle-shaped point, but in some instances are formed with a sharpened knife edge to allow the surgeon to make nonelectrical incisions. In some electrodes, the metal conductive portion is formed of malleable metal material so that it can be bent by the surgeon to any desired shape to suit the task to be performed. Referring to FIG. 2, an electrode 30 with a downwardly curved tip portion 32 is disclosed.

In typical use, electrode holder 14 is gripped by the surgeon, electrode tip 24 placed in contact or near contact with the work surface on the patient's body where cutting, coagulation, fulguration or desiccation is to take place, and switch 18 actuated to cause a high frequency current to pass to the patient's body. A description of the operation of an electrosurgical device is set forth in the background portion of U.S. Pat. No. 4,562,838, and this description is incorporated herein by reference. As set out therein the current density and resistance at the tip of the electrode are at their maximum, generating enough heat in tissue for vaporization and pyrolysis.

When vaporization of tissue occurs, besides generating unwanted smoke as discussed in U.S. Pat. No. 4,562,838, it has been found that blood and tissue of the patient are caused to spray and splatter in a random fashion away from the work surface. In the past, a portion of the spray and splatter has often come in contact with the face and eyes of the surgeon operating the electrosurgical unit or his assistant.

As illustrated in FIG. 1, the present invention provides a shield 34 that is adapted to be mounted such that a transparent barrier 36 is positioned generally adjacent electrode tip 24 and between the work surface on the patient's body and the surgeon. Shield 34 also includes a mounting means 38 incorporated in a transverse end wall 40 for mounting of the shield on the electrode, the electrode insulator, or on the tip portion of the electrode holder. It will be understood that the exact point at which the spray shield is mounted or the structure on which it is mounted is not critical so long as the transparent barrier portion of the shield is positioned generally adjacent the electrode tip 24.

Referring additionally to FIGS. 3 and 4, the relative location of electrode tip 24 with respect to the transparent barrier 36 is illustrated. It will be understood that by modifying the location at which the spray shield is mounted on the electrode, its conductor, or the electrode holder, the relative location of the tip of the electrode 24 and transparent barrier 36 may be adjusted. As illustrated, the electrode tip is positioned slightly below the spray shield and generally adjacent its end, such that the electrode may be freely moved into position in contact with the patient's skin without interference caused by the spray shield itself contacting the patient. It will be understood that if the shield is positioned so that it extends a substantial distance beyond electrode tip 24, that the end of the shield is likely to come into contact with the patient during a cutting or coagulating operation where the electrode holder is held in a manner similar to the way in which one holds a pen. Likewise, if tip 24 extends a substantial distance beyond the end of the transparent barrier 36, the shield's ability to capture spray and splatter from the work surface will be correspondingly diminished. The exact positioning of the shield with respect to the electrode tip is a matter of discretion for the user and that the shield may extend a small distance beyond the electrode tip if desired.

Referring again to FIG. 1, the transparent barrier portion of the spray shield 36 is shown to be arcuately curved transversely along the length of electrode 24. In this configuration, the shield is able to capture a substantial portion of the spray and splatter emanating from the work surface without having to extend laterally to such a distance that the size of the shield makes it likely to interfere with use of the electrode. It will be understood, however, that this transverse curve is not critical to the invention and that the barrier could also be made flat with a different curvature.

Referring additionally to FIG. 3, it will be seen that the lateral edges 42 and 44 of the transparent barrier are flared outwardly near the working end of the electrode by flattening of the transverse curvature of the transparent barrier. It will be understood that other barrier shapes may also be satisfactorily used so long as the goal of interposing the transparent spray shield between the electrode tip 24 in contact with the patient's skin and the face of the surgeon is accomplished.

In one embodiment, it has been found that the shield may be satisfactorily formed of a durable, transparent polycarbonate material. Shields formed of this material may be sterilized and, thus, the shield may be reused. In general, however, it is contemplated that the shield and the possibly contaminated splattered blood and tissue that coats the undersurface of the shield after use will be disposed of after a single use. The shield may be formed of any suitable material of a transparent nature, it being preferred that the material be sterilizable at least prior to the initial use so that the possibility of wound contamination is eliminated should the shield accidentally come in contact with the patient during use. A material that may readily be cut with scissors has been considered for use, it being contemplated that the spray shield may be initially formed to be of a longer length than normally needed with the surgeon cutting the shield to a desired length prior to use. In this way, the shield could likely be used with a very wide variety of electrode shapes and sizes and could also be used more conveniently by surgeons for a wider variety of tasks. For example, a surgeon might first cut the shield to a certain length that would be suitable for blocking blood spray and tissue splatter when making an initial incision. Thereafter, however, when cutting or cauterizing within an incision, and possibly using a different shaped electrode, the surgeon might choose to cut the shield to a shorter or narrower shape to prevent contact between the shield and the walls of the incision.

Referring additionally to FIG. 2, the spray shield 46 is disclosed having a transparent barrier portion 48 that is longitudinally curved or angled along transverse line 50 to generally follow the curve of electrode 22. Use of a longitudinally curved spray shield allows the shield to remain relatively close to working tip 24 to capture a greater portion of the blood spray or tissue splatter from the work surface than would be the case if the transparent barrier portion continued to extend straight while the electrode tip curved away from it. It will be understood that in such a situation the barrier shield would intercept a smaller segment of the arc through which spray and splatter may be propelled from the work area. As shown in FIG. 2, the end portion of the transparent barrier is again positioned substantially adjacent to, but spaced from, working tip 24 to allow for substantial capture of spray and splatter while still leaving the electrode tip free to be used without interference caused by the spray shield contacting the patient's body.

Finally, referring to FIG. 5, end wall 40 is shown to extend transversely to the curved transparent barrier portion 36 of the spray shield. As illustrated, the end wall 40 includes a mounting means 38 comprising a generally figure eight shaped opening including an upper, generally circular opening 52 and a lower, generally circular opening 54 of larger diameter than opening 52. An introit 56 with inwardly sloping walls 58 is positioned along the lower edge of wall 40 and is adapted to lead a circular electrode, electrode insulator, or portion of an electrode holder on which the spray shield is to be mounted into opening 54. It will be understood that in the disclosed embodiment, the materials of which the spray shield is formed are somewhat resilient, such that walls 58 will spread apart as the spray shield is pushed onto the electrode or the like, and then snap back once the electrode is positioned within opening 54 to thereby resiliently hold the spray shield onto the electrode.

If the electrode upon which the spray shield is to be mounted is of substantially smaller diameter than opening 54, the spray shield may be pressed further onto the electrode until it passes through channel 60 and into opening 52. Again, the resilient nature of the materials of which the spray shield are made cause the walls of opening 52 to grip the electrode to retain the shield in place.

It will be understood that openings 50 and 52 may be formed of differing sizes or shapes to accommodate differently sized or shaped electrodes, or that a single opening or an opening of different shape adapted to accommodate a variety of electrode, electrode insulator, or electrode holder diameters may also be used. In general, any suitable means for holding the transparent barrier portion of the spray shield adjacent the working tip of the electrode may be used and are considered to be within the scope of this invention.

Although the present invention has been disclosed with respect to several preferred embodiments and modifications thereto, further modifications will be apparent to those skilled in the art. Accordingly, it is not intended that the invention be limited by the disclosure or by such modifications, but instead that its scope should be determined entirely by reference to the claims which follow hereinbelow.

The embodiments of the invention in which an exclusive property or privilege is claimed are defined as follows:

1. A spray shield for an electrosurgical unit having an electrode extending from a holder comprising:
   transparent barrier means, positioned between the electrode and the operator of the electrosurgical unit during use when the electrode contacts a work area on a patient for capturing a portion of the matter emanating from the work surface, said barrier means transversely subtending an angle of at least 45° about the electrode; and
   mounting means integral with said barrier means for mounting said spray shield on said electrosurgical unit to hold said spray shield in said position between the electrode and the operator during use of the electrosurgical unit.

2. The spray shield of claim 1 wherein said transparent barrier means extends longitudinally along said electrode to a point substantially adjacent to but spaced from the electrode tip.

3. The spray shield of claim 1 wherein said transparent barrier means extends longitudinally along said electrode toward the tip of the electrode and is curved transversely to partially surround said electrode and tip.

4. The spray shield of claim 1 wherein said electrode is curved along a longitudinal axis thereof and said spray shield is correspondingly curved to allow said transparent barrier means to be positioned between the patient contacting tip of the electrode on said work area and said operator.

5. The spray shield of claim 1 wherein said spray shield is made of electrically nonconductive material.

6. The spray shield of claim 1 wherein said mounting means comprises resilient clamping means for gripping said electrode.

7. The spray shield of claim 6 wherein said mounting means comprises means extending transversely from said transparent barrier means distal from the end of said barrier means adjacent a tip of the electrode; said means including opening means for resiliently engaging said electrode.

8. The spray shield of claim 7 wherein said mounting means includes opening means sized to resiliently engage electrodes of differing diameter.

9. A device for intercepting spray or splatter of blood or tissue produced during contact of the tip of an electrode of an electrosurgical unit with the skin or other body portion of a patient to prevent the spray or splatter from being deposited on the user of the electrosurgical unit, comprising:
   a transparent barrier removably mounted on said electrosurgical unit and extending adjacent the patient contacting electrode tip and between said tip and the user of the electrosurgical unit for capturing a portion of the matter emanating from the work surface, said barrier means transversely subtending an angle of at least 45° about the electrode.

10. The device of claim 9, wherein said transparent barrier is formed of a material that may be sterilized prior to use.

11. The device of claim 9, including means for mounting said transparent barrier means adjacent said electrode tip comprising resilient means for engaging said electrode.

12. The device of claim 9, wherein said transparent barrier means extends longitudinally along said electrode toward the tip of the electrode and is curved transversely to partially surround said electrode and tip.

13. A spray shield for an electrosurgical unit having an electrode extending from a holder, comprising:
   transparent barrier means adapted to be positioned between the electrode and the operator of the electrosurgical unit during use when the electrode contacts a work area on a patient, said transparent barrier means extending longitudinally along said electrode toward a tip of the electrode and curved transversely to partially surround said electrode and tip; and
   mounting means integral with said barrier means for mounting said spray shield on said electrosurgical unit to hold said spray shield on said electrosurgical unit in said position between the electrode and the operator during use of the electrosurgical unit.

14. The spray shield of claim 13, wherein the electrode is curved along a longitudinal axis thereof, and said spray shield is correspondingly curved to allow said transparent barrier means to be positioned between the patient contacting tip of the electrode on the work area and the operator.

15. The spray shield of claim 13, wherein said spray shield is made of electrically nonconductive material.

16. The spray shield of claim 13, wherein said mounting means comprises resilient clamping means adapted to grip the electrode.

17. The spray shield of claim 16, wherein said mounting means comprises means extending transversely from said transparent barrier means distal from the end of said barrier means adjacent the tip of the electrode, and said means includes opening means adapted to resiliently engage the electrode.

18. The spray shield of claim 17, wherein said mounting means includes opening means sized to resiliently engage electrodes of differing diameters.

19. A spray shield for an electrosurgical unit having an electrode extending from a holder, comprising:
transparent barrier means for positioning between the electrode and the operator of the electrosurgical unit during use when the electrode contacts a work area on a patient; and
mounting means integral with said barrier means adapted to mount said spray shield on the electrode to hold said spray shield in position between the electrode and the operator during use of the electrosurgical unit, said mounting means extending transversely from said transparent barrier means distal from an end of said barrier means adjacent a tip of the electrode and said mounting means including opening means sized to resiliently engage electrodes of differing diameter.

20. The spray shield of claim 19, wherein said transparent barrier means extends longitudinally along said electrode to a point adjacent to but spaced from the electrode tip.

21. The spray shield of claim 19, wherein said transparent barrier means extends longitudinally along the electrode toward the tip of the electrode and is curved transversely to partially surround the electrode and tip.

22. The spray shield of claim 19, wherein the electrode is curved along a longitudinal axis thereof and said spray shield is correspondingly curved to allow said transparent barrier means to be positioned between the patient contacting tip of the electrode on the work area and the operator.

* * * * *